(12) United States Patent
Obot et al.

(10) Patent No.: US 11,118,272 B2
(45) Date of Patent: Sep. 14, 2021

(54) HETEROCYCLIC CORROSION INHIBITOR COMPOUNDS AND USES THEREOF

(71) Applicant: King Fahd University of Petroleum and Minerals, Dhahran (SA)

(72) Inventors: Ime Bassey Obot, Dhahran (SA); Benedict Ikenna Onyeachu, Dhahran (SA); Mumtaz Ahmad Quraishi, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 16/376,819

(22) Filed: Apr. 5, 2019

(65) Prior Publication Data
US 2020/0318243 A1    Oct. 8, 2020

(51) Int. Cl.
*C23F 11/16* (2006.01)
*C07D 487/04* (2006.01)

(52) U.S. Cl.
CPC .......... *C23F 11/162* (2013.01); *C07D 487/04* (2013.01)

(58) Field of Classification Search
CPC ............................ C23F 11/162; C07D 487/04
See application file for complete search history.

(56) References Cited

U.S. PATENT DOCUMENTS 4,187,277 A * 2/1980 Quinlan .................. C23F 11/04
422/16

OTHER PUBLICATIONS

Kategaonkar et al. Microwave assisted synthesis of pyrimido[4,5-d]pyrimidine derivatives in dry media, 2009, Ukrainica Bioorganica Acta 1 p. 3-7 (Year: 2009).*

Huwaida M.E. Hassaneen and Ismail A. Abdelhamid "One-Pot Synthesis of 5-Unsubstituted-6-Aroyl[1,2,4]triazolo[1,5-a]pyrimidine Utilizing Biginelli-Like Multicomponent Reaction of Enaminones with 3-Amino-1,2,4-triazole as the Urea Component" 2013 Current Organic Synthesis 10 p. 953-955 (Year: 2013).*

Giribala M. Bondle and Sandeep T. Atkore "Green approach for synthesizing Pyrimido pyrimidine moieties using TBAB" 2016 Journal of Chemical and Parmaceutical Research 8(7) pp. 717-721 (Year: 2016).*

Jiyaul Hague, K.R. Ansari, Vandana Srivastava, M.A. Quraishi, I.B. Obot "Pyrimidine derivatives as novel acidizing corrosion inhibitors for N80 steel useful for petroleum industry: A combined experimental and theoretical approach" 2017 Journal of Industrial and Engineering Chemistry pp. 176-188 (Year: 2017).*

Shirini, et al. ; Preparation and characterization of [H-DABCO][CIO ] as a new member of DABCO-based ionic liquids for the synthesis of pyrimido[4,5-b]-quinoline and pyrimido [4,5-d]pyrimidine derivatives ; Journal of Molecular Structure, vol. 1161 ; pp. 366-382 ; Jun. 5, 2018 ; Abstract Only ; 3 Pages.

(Continued)

*Primary Examiner* — Andrew J. Oyer
(74) *Attorney, Agent, or Firm* — Obion, McClelland, Maier & Neustadt, L.L.P.

(57) ABSTRACT

Heterocyclic compounds having fused pyrimidine moieties with electron-donating groups. A method of preparing the heterocyclic compounds via a multicomponent condensation reaction is specified. These compounds are effective against corrosion of metallic substrates in acidic (i.e. $CO_2$), and high salinity environments commonly found in oil and gas industry.

11 Claims, 6 Drawing Sheets

(56) References Cited

OTHER PUBLICATIONS

Haque, et al. ; Pyrimidine derivatives as novel acidizing corrosion inhibitors for N80 steel useful for petroleum industry: A combined experimental and theoretical approach ; Journal of Industrial and Engineering Chemistry, vol. 49 ; pp. 176-188 ; May 25, 2017 ; Abstract Only ; 2 Pages.

Aly, et al. ; Utility of a Pyrimidine Thione Derivative in the Synthesis of New Fused Pyrimido[4,5-D] Pyrimidine, Pyrido[2,3-D]Pyrimidine and Different Types of Thienopyrimidine Derivatives ; International Journal of Advanced Research ; Apr. 30, 2014 ; Abstract Only ; 2 Pages.

Al-Harbi, et al. ; Synthesis of Some New Fluorine Substituted Thiobarbituricacid Derivatives as Anti HIV1 and Cyclin-Dependent Kinase 2 (CDK2) for Celltumer Division—Part II ; International Journal of Organic Chemistry 4 ; pp. 142-153 ; Jun. 19, 2014 ; 13 Pages.

Mobinikhaledi, et al. ; Triethyl benzyl ammonium chloride (TEBAC) catalyzed solvent-free one-pot synthesis of pyrimido[4,5-d]pyrimidines ; Research on Chemical Intermediates, vol. 41, Issue 5 ; pp. 2985-2990 ; Oct. 4, 2013 ; 7 Pages ; Abstract Only.

Faidallah, et al. ; Synthesis and biological evaluation of new barbituric and thiobarbituric acid fluoro analogs of benzenesulfonamides as antidiabetic and antibacterial agents ; Journal of Fluorine Chemistry vol. 142 ; pp. 96-104 ; Oct. 2012 ; Abstract Only ; 3 Pages.

Dabholkar, et al. ; Synthesis of biginelli products of thiobarbituric acids and their antimicrobial activity ; Journal of the Serbian Chemical Society, vol. 75, Issue 8 ; pp. 1033-1040 ; 2010 ; Abstract Only ; 2 Pages.

Sharma, et al. ; Synthesis and Evaluation of Antimicrobial Activity of Novel Hydrazino and NBenzylidinehydrazino-Substituted 4,8-Dihydro-1H,3H-pyrimido[4,5-d]pyrimidin-2,7-dithiones ; Archiv der Pharmazie, vol. 339, Issue 10 ; Sep. 28, 2006 ; Abstract Only ; 2Pages.

Kidwai, et al. ; Solid-supported Hantzsch-Biginelli reaction for syntheses of pyrimidine derivatives ; Russian Chemical Bulletin, vol. 52, Issue 11 ; p. 2457 ; Nov. 2003 ; Abstract Only ; 4 Pages.

* cited by examiner

HETEROCYCLIC CORROSION INHIBITOR COMPOUNDS AND USES THEREOF

BACKGROUND OF THE INVENTION

Technical Field

The present disclosure relates to heterocyclic compounds that inhibit or alleviate corrosion of metallic substrates in corrosive media and methods thereof. More specifically, the present disclosure relates to heterocyclic compounds containing fused pyrimidine-based moieties with electron-donating groups for arresting metal corrosion, methods of synthesizing the compounds, and methods of preventing metal corrosion using the compounds.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Steel is a commonly used material for the construction of pipelines, tubing, and storage tanks in the oil and gas industry [A. Yousefi, S. Javadian, N. Dalir, et al., Imidazolium-Based Ionic Liquids as Modulators of Corrosion Inhibition of SDS on Mild Steel in Hydrochloric Acid Solutions: Experimental and Theoretical Studies, RSC Advances 5 (2015) 11697-11713; and M. Tourabi, K. Nohair, M. Traisnel, et al., Electrochemical and XPS Studies of the Corrosion Inhibition of Carbon Steel in Hydrochloric Acid Pickling Solutions by 3,5-bis(2-thienylmethyl)-4-amino-1,2,4-triazole, Corrosion Science 75 (2013) 123-133]. However, steel often degrades due to $CO_2$-induced corrosion. The practice of enhanced oil recovery (EOR) is frequently employed in the petroleum industry during offshore drilling in order to maximize output of crude oil and natural gas from parent rock materials. A well-established method for performing EOR involves simultaneously injecting $CO_2$ gas with drilling brine solution under high pressure. $CO_2$ is a preferred gas for EOR because of its cost effectiveness and high miscibility with crude oil and natural gases [A. Ikeda, S. Mukai, M. Ueda, Corrosion behavior of 9 to 25% Cr steels in wet $CO_2$ environments, Corrosion 41 (1985) 185-192; and X. Jiang, Y. G. Zheng, D. R. Qu, W. Ke, Effect of calcium ions on pitting corrosion and inhibition performance in $CO_2$ corrosion of N80 steel, Corrosion Science 48 (2006) 3091-3108].

The electrochemistry of $CO_2$-induced corrosion initially involves the dissolution of $CO_2$ gas in the aqueous phase of a drilling solution to form a weak carbonic acid ($H_2CO_3$). This is followed by several cathodic half-reactions depending on the prevalent pH of the aqueous environment [S. Nesic, J. Postlethwaite, S. Olsen, An electrochemical model for prediction of corrosion of mild steel in aqueous carbon dioxide solutions, Corrosion 52 (1996) 280-294]. The principal anodic half-reaction is the oxidation of iron (Fe) atoms into iron (II) ($Fe^{2+}$) ions. These processes are shown in the following equations:

$$CO_{2(g)} + H_2O_{(l)} \leftrightharpoons H_2CO_{3(aq)} \qquad (1)$$

Cathodic reactions: $2H_2CO_{3(aq)} + 2e^- \rightarrow H_{2(g)} + 2HCO_{3(aq)}^-$; (pH 4-6) (2)

$2HCO_{3(aq)}^- + 2e^- \rightarrow H_{2(g)} + 2CO_{3(aq)}^{2-}$; (pH≥6) (3)

$2H^+_{(aq)} + 2e^- \rightarrow H_{2(g)}$; (pH<4) (4)

Anodic reaction: $Fe_{(s)} \rightarrow Fe_{(aq)}^{2+} + 2e^-$ (5)

Incorporating corrosion inhibitors into drilling solutions may significantly lower the rate of $CO_2$-induced corrosion of steel. For this purpose, heterocyclic compounds such as imidazolines, [A. H. Mustafa, B. Ari-Wahjoedi, M. C. Ismail, Inhibition of $CO_2$ corrosion of X52 steel by imidazoline-based inhibitor in high pressure $CO_2$-water environment, Materials Engineering & Performance 22 (2013) 1748-1755; V. Jovancicevic, S. Ramachandran, P. Prince, Inhibition of carbon dioxide corrosion of mild steel by imidazolines and their precursors, Corrosion 55(1999) 449-455; F. Farelas, A. Ramirez, Carbon dioxide corrosion inhibition of carbon steels through bis-imidazoline and imidazoline compounds studied by EIS, Int. J. Electrochemical Science 5 (2010) 797-814; Y. Xiong, B. Brown, B. Kinsella, et al., Atomic force microscopy study of the adsorption of surfactant corrosion inhibitor films, Corrosion 70 (2014) 247-260; R. Zamudio, A. Estrada, A. Benavides, et al., Corrosion control of carbon steel in sulfuric acid environment by 1-(2-hydroxyethyl)-2-alkylimidazolines and its corresponding amide precursors, Revista de la Sociedad Química de México 46 (2002) 335-340; P. C. Okafor, X. Liu, Y. G. Zheng, Corrosion inhibition of mild steel by ethylamino imidazoline derivative in $CO_2$-saturated solution, Corrosion Science 51 (2009) 761-768; and D. A. Lopez, S. N Simison, S. R De Sanchez, Inhibitors performance in $CO_2$ corrosion: EIS studies on the interaction between their molecular structure and steel microstructure, Corrosion Science 47 (2005) 735-755, each incorporated herein by reference in their entirety], triazoles [S. Ghareba, S. Omanovic, Interaction of 12-aminododecanoic acid with a carbon steel surface: Towards the development of green corrosion inhibitors, Corrosion Science 52 (2010) 2104-2113; and R. Olalde, J. Genesca, Effect of flow and a triazole derivative based inhibitor on the corrosion of API X52 pipeline steel grade in $CO_2$ saturated brine solution, ECS Transactions 20 (2009) 529-541, each incorporated herein by reference in their entirety], and amines [X. Jiang, Y. G. Zheng, W. Ke, Corrosion inhibitor performances for carbon dioxide corrosion of N80 steel under static and flowing conditions, Corrosion 61 (2005) 326-334; and M. P. Desimone, G. Grundmeier, G. Gordillo, et al., Amphiphilic amido-amine as an effective corrosion inhibitor for mild steel exposed to $CO_2$ saturated solution: Polarization, EIS and PM-IRRAS studies, Electrochimica Acta 56 (2011) 2990-2998, each incorporated herein by reference in their entirety] have been tested and utilized as acid corrosion inhibitors. These inhibitors can be adsorbed onto the metal surface through lone pairs of electrons donated by nitrogen atoms, thereby forming an inhibitor film on the metal surface which isolates the surface from acidic media and lowers the corrosion rate. The most researched and commercially available corrosion inhibitors are toxic in nature. Therefore, efforts have been made towards the research and development of environmentally benign corrosion inhibitors.

Pyrimidine derivatives are nitrogen-containing heterocyclic compounds that exhibit biological activities including antiviral, antibacterial, antioxidant, and anti-allergy properties [K. S. Jain, T. S. Chitre, P. B. Miniyar, et al., Biological and medicinal significance of pyrimidines, Current Science 90 (2006) 793-803, incorporated herein by reference in its entirety]. A few pyrimidines have been reported as good corrosion inhibitors for steel corrosion in acid media such as oilfield environments [C. Verma, L. O. Olasunkanmi, E. E. Ebenso, et al., Adsorption behavior of glucosamine-based, pyrimidine-fused heterocycles as green corrosion inhibitors for mild steel: Experimental and theoretical studies, J. Physical Chemistry C 120 (2016) 11598-11611; K. R. Ansari, Sudheer, A. Singh, M. A. Quraishi, Some pyrimidine derivatives as corrosion inhibitors for mild steel in hydrochloric acid, J. Dispersion Science & Technology 36 (2015) 908-917; J. Hague, K. R. Ansari, V. Srivastava, et al., Pyrimidine derivatives as novel acidizing corrosion inhibitors for N80 steel useful for petroleum industry: A combined experimental and theoretical approach, J. Industrial & Engineering Chemistry 49 (2017) 176-188; C. Verma, L. O. Olasunkanmi, E. E. Ebenso, et al., Adsorption characteristics of green 5-arylaminomethylene pyrimidine-2,4,6-triones on mild steel surface in acidic medium: Experimental and computational approach, Results in Physics 8 (2018) 657-670; and C. Verma, M. A. Quraishi, K. Kluza, et al., Corrosion inhibition of mild steel in 1M HCl by D-glucose derivatives of dihydropyrido [2,3-d:6,5-d']dipyrimidine-2,4, 6, 8(1H,3H,5H,7H)-tetraone, Scientific Reports 7 (2017) 44432, each incorporated herein by reference in their entirety]. Despite these recent advances there is still a need to develop more efficient pyrimidine compounds based on nontoxic, cheap, and readily available substrates using environmentally friendly chemistry.

In view of the forgoing, one objective of the present disclosure is to provide corrosion inhibitor compounds and their methods of synthesis. A further objective of the present disclosure is to provide methods for preventing or inhibiting metal corrosion commonly found in oil and gas industry using the corrosion inhibitor compounds.

BRIEF SUMMARY OF THE INVENTION

According to a first aspect, the present disclosure relates to a compound of formula (I)

(I)

or a salt thereof, a solvate thereof, a tautomer thereof, a stereoisomer thereof, or a mixture thereof wherein i) $R_1$ is selected from the group consisting of an optionally substituted alkoxy, an optionally substituted aryloxy, an optionally substituted amino, and an optionally substituted amide, ii) each $R_2$ is independently selected from the group consisting of a hydrogen, an optionally substituted alkyl, an optionally substituted cycloalkyl, an optionally substituted arylalkyl, and an optionally substituted aryl, iii) each $R_3$ is independently selected from the group consisting of a hydrogen, an optionally substituted alkoxy, an optionally substituted aryloxy, an optionally substituted amino, an optionally substituted amide, an optionally substituted alkyl, an optionally substituted cycloalkyl, an optionally substituted arylalkyl, and an optionally substituted aryl, iv) X is O or S, and v) Y is O or S.

In one embodiment, $R_1$ is $-NH_2$, a $(C_{1-6})$alkylamino, or a di$(C_{1-6})$alkylamino.

In one embodiment, $R_1$ is selected from the group consisting of $-NH_2$, $-NHCH_3$, $-NHC_2H_5$, $-N(CH_3)_2$, $-N(CH_3)C_2H_5$, $-N(C_2H_5)_2$, pyrrolidinyl, piperidinyl, 4-methylpiperidinyl, morpholinyl, piperazinyl, and (N-methyl)piperazinyl.

In one embodiment, $R_1$ is $-N(CH_3)_2$.
In one embodiment, each $R_2$ is a hydrogen.
In one embodiment, each $R_3$ is a hydrogen.
In one embodiment, X is S.
In one embodiment, Y is S.
In one embodiment, the compound of formula (I) is According to a second aspect, the present disclosure relates to a method of inhibiting corrosion of a metallic substrate in contact with a corrosive medium. The method involves introducing the compound of formula (I) of the first aspect into the corrosive medium in contact with the metallic substrate.

In one embodiment, the compound of formula (I) is

In one embodiment, the metallic substrate comprises steel.

In one embodiment, the metallic substrate comprises carbon steel.

In one embodiment, the corrosive medium comprises at least one inorganic acid, at least one inorganic salt, or both.

In one embodiment, the corrosive medium comprises $CO_2$, brine, or both.

In one embodiment, the corrosive medium has a pH of 5 or below.

In one embodiment, the compound of formula (I) is introduced into the corrosive medium at a concentration of 0.1-200 ppm.

In one embodiment, the method has a corrosion inhibition efficiency in a range of 85-98%.

In one embodiment, the compound of formula (I) imparts a corrosion rate in a range of 0.8-2.5 mils penetration per year (mpy) to the metallic substrate.

In one embodiment, the metallic substrate is part of a system for oil or gas production, transportation, or refining.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Embodiments of the present disclosure will now be described more fully hereinafter with reference to the accompanying drawings, in which some, but not all embodiments of the disclosure are shown.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the terms "compound" and "product" are used interchangeably, and are intended to refer to a chemical entity, whether in the solid, liquid or gaseous phase, and whether in a crude mixture or purified and isolated.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, iso-propanol, n-butanol, iso-butanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the ring systems, stereogenic centers, and the like can all be present in the compounds, and all such stable isomers are contemplated in the present disclosure. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

The present disclosure is intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}C$ and $^{14}C$, isotopes of nitrogen include $^{15}N$, isotopes of oxygen include $^{17}O$ and $^{18}O$, and isotopes of sulfur include $^{33}S$, $^{34}S$, and $^{36}S$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyridyl, pyrimidiyl, and the like), substituted heterocyclyl and mixtures thereof and the like. The substituents may themselves be optionally substituted, and may be either unprotected, or protected as necessary, as known to those of ordinary skill in the art, for example, as taught in Greene, et al., "Protective Groups in Organic Synthesis", John Wiley and Sons, Second Edition, 1991, hereby incorporated by reference in its entirety.

As used herein, the term "an optionally substituted amine" includes unsubstituted amine (—NH$_2$), monosubstituted amine (—NHR$_a$), as well as disubstituted amine (—NR$_a$R$_b$), wherein R$_a$ and R$_b$ are independently an optionally substituted alkyl, an optionally substituted cycloalkyl, an optionally substituted arylalkyl, or an optionally substituted aryl.

Disubstituted amines which are cyclic disubstituted amines are also contemplated as part of the disubstituted amine family, where R$_a$ and R$_b$ together form a cyclic ring with the nitrogen atom to which they are attached, thereby forming for example a 3-membered, 4-membered, 5-membered, 6-membered, 7-membered, or 8-membered ring. Exemplary cyclic dialkylamines include, but are not limited to, pyrolidyl piperidinyl

4-methylpiperidinyl morpholinyl piperazinyl (N-methyl)piperazinyl and homopiperazinyl

The term "amide", as used herein, and unless otherwise specified, refers to an amide (—C(O)NR$_c$R$_d$) that is unsubstituted (—C(O)NH$_2$), optionally monosubstituted (where R$_c$ is a hydrogen), or disubstituted where R$_c$ and R$_d$ are independently an optionally substituted alkyl, an optionally substituted cycloalkyl, an optionally substituted arylalkyl, or an optionally substituted aryl.

As used herein, the term "alkyl" unless otherwise specified refers to both branched and straight chain saturated aliphatic primary, secondary, and/or tertiary hydrocarbons of typically C$_1$ to C$_{21}$, for example C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

As used herein, the term "aryl" unless otherwise specified refers to functional groups or substituents derived from an aromatic ring including, but not limited to, phenyl, biphenyl, napthyl, anthracenyl, thienyl, and indolyl. As used herein, the term optionally includes both substituted and unsubstituted moieties. Exemplary moieties with which the aryl group can be substituted may be selected from the group including, but not limited to, hydroxy, amino, alkylamino, arylamino, alkoxy, aryloxy, nitro, cyano, sulfonic acid, sulfate, phosphonic acid, phosphate or phosphonate or mixtures thereof. The substituted moiety may be either protected or unprotected as necessary, and as known to those skilled in the art.

The term "alkoxy" refers to a straight or branched chain alkoxy including, but not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

The term "aryloxy" refers to an aryl group bonded to an oxygen atom. Exemplary aryloxy groups include, but are not limited to, phenoxy, 4-methylphenoxy, and naphthaloxy.

According to a first aspect, the present disclosure relates to a compound of formula (I)

(I)

or a salt thereof, a solvate thereof, a tautomer thereof, a stereoisomer thereof, or a mixture thereof.

R$_1$ is selected from the group consisting of an optionally substituted alkoxy, an optionally substituted aryloxy, an optionally substituted amino, and an optionally substituted amide. In one embodiment, R$_1$ is —NH$_2$. In another embodiment, R$_1$ is an alkylamino, preferably a (C$_{1-8}$)alkylamino, preferably a (C$_{2-7}$)alkylamino, preferably a (C$_{3-6}$)alkylamino, preferably a (C$_{4-5}$)alkylamino, such as —NHCH$_3$, and —NHC$_2$H$_5$. In a preferred embodiment, R$_1$ is a dialkylamino, preferably a di(C$_{1-8}$)alkylamino, preferably a di(C$_{2-7}$)alkylamino, preferably a di(C$_{3-6}$)alkylamino, preferably a di(C$_{4-5}$)alkylamino, such as —N(CH$_3$)$_2$, —N(CH$_3$)C$_2$H$_5$, —N(C$_2$H$_5$)$_2$, pyrrolidinyl, piperidinyl, 4-methylpiperidinyl, morpholinyl, piperazinyl, and (N-methyl)piperazinyl. In a most preferred embodiment, R$_1$ is —N(CH$_3$)$_2$.

Each R$_2$ is independently selected from the group consisting of a hydrogen, an optionally substituted alkyl, an optionally substituted cycloalkyl, an optionally substituted arylalkyl, and an optionally substituted aryl. In one embodiment, each R$_2$ is independently selected from the group consisting of a hydrogen, a methyl, an ethyl, a n-propyl, an isopropyl, an n-butyl, a tert-butyl, and a sec-butyl. In a preferred embodiment, each R$_2$ is a hydrogen.

Each R$_3$ is independently selected from the group consisting of a hydrogen, an optionally substituted alkoxy, an optionally substituted aryloxy, an optionally substituted amino, an optionally substituted amide, an optionally substituted alkyl, an optionally substituted cycloalkyl, an optionally substituted arylalkyl, and an optionally substituted aryl. In one or more embodiments, each R$_3$ is independently selected from the group consisting of a hydrogen, a methoxy, an ethoxy, a methyl, an ethyl, a n-propyl, an isopropyl, an n-butyl, a tert-butyl, and a sec-butyl. In a preferred embodiment, each R$_3$ is a hydrogen.

The element X may be O or S. In a preferred embodiment, X is S.

The element Y may be O or S. In a preferred embodiment, Y is S.

In one or more embodiments, the compound of formula (I) is

The compounds of the present disclosure may be prepared by methods known to those of ordinary skills in the art. The following methods set forth below are provided for illustrative purposes and are not intended to limit the scope of the disclosure.

In one embodiment, a method of synthesizing the compound of formula (I) of the first aspect involves mixing an aldehyde of formula (II)

(II)

or a salt, solvate, or stereoisomer thereof, with a compound of formula (III)

(III)

or a salt, solvate, or tautomer thereof and a compound of formula (IV)

(IV)

or a salt, solvate, or tautomer thereof in the presence of an acid and optionally a solvent to form a reaction mixture, and heating the reaction mixture thereby forming the compound of formula (I), wherein $R_1$, $R_2$, $R_3$, X, and Y are as previously specified.

In a preferred embodiment, reacting the aldehyde of formula (II) with the compound of formula (III) and the compound of formula (IV) in the presence of an acid to form the compound of formula (I) is performed in a polar solvent, preferably in ethanol (EtOH). Exemplary additional polar solvents that may be used in addition to, or in lieu of ethanol include, but are not limited to, methanol, n-butanol, isopropanol, n-propanol, tetrahydrofuran, ethyl acetate, acetone, acetonitrile, dimethyl sulfoxide, nitromethane and propylene carbonate, or mixtures thereof. It is equally envisaged that the reaction may be adapted to be performed in a non-polar solvent (i.e. pentane, cyclopentane, hexane, cyclohexane, benzene, toluene, 1,4-dioxane, chloroform, diethyl ether, dichloromethane, and mixtures thereof). In certain embodiments, reacting the aldehyde with the compound of formula (III) and the compound of formula (IV) in the presence of an acid is conducted in neat (solvent-free) conditions.

In a preferred embodiment, the reaction is performed at a concentration of the aldehyde of formula (II) in the range of 0.01-50 M, preferably 0.1-25 M, preferably 0.5-10 M, preferably 1-8 M, preferably 2-5 M. In a preferred embodiment, the reaction is performed at a concentration of the compound of formula (III) in the range of 0.01-50 M, preferably 0.1-25 M, preferably 0.5-10 M, preferably 1-8 M, preferably 2-5 M. In a preferred embodiment, the reaction is performed at a concentration of the compound of formula (IV) 0.01-50 M, preferably 0.1-25 M, preferably 0.5-10 M, preferably 1-8 M, preferably 2-5 M. In one or more embodiments, a molar ratio of the compound of formula (III) to the aldehyde of formula (II) is in the range of 1:3 to 3:1, preferably 1:2 to 2:1, preferably 2:3 to 3:2, or about 1:1. In one or more embodiments, a molar ratio of the compound of formula (III) to the compound of formula (IV) is in the range of 1:3 to 3:1, preferably 1:2 to 2:1, preferably 2:3 to 3:2, or about 1:1.

Exemplary acids that may be suitable for the reaction described herein include, without limitation, hydrochloric acid (HCl), sulfuric acid, phosphoric acid, sulfamic acid, fluoroboric acid, hexafluorophosphoric acid, acetic acid, fluoroacetic acid, chloroacetic acid, dichloroacetic acid, trifluoroacetic acid, trichloroacetic acid, propionic acid, formic acid, citric acid, citrate acid, oxalate acid, benzoic acid. Preferably, HCl is employed as the acid. HCl used herein may be present as an aqueous solution containing 5-16 M HCl, preferably 10-14 M HCl, or 12-13 M HCl relative to a total volume of the aqueous solution. Alternatively, a mixture having HCl in other polar solvent such as methanol, ethanol, 2-propanol, and 1-butanol may be used. In one embodiment, the acid is present at a concentration of 0.001-2 M, preferably 0.01-1 M, preferably 0.05-0.8 M, preferably 0.1-0.5 M, preferably 0.2-0.4 M relative to a total volume of the reaction mixture.

In one or more embodiments, the reaction mixture is heated at a temperature of 30-150° C., preferably 40-120° C., preferably 50-100° C., preferably 60-90° C., preferably 70-80° C. for 0.1-10 hours, preferably 0.25-8 hours, preferably 0.5-6 hours, preferably 1-5 hours, preferably 2-4 hours. An external heat source, such as a water bath or an oil bath, an oven, microwave, or a heating mantle, may be employed to heat the reaction mixture. In some embodiments, the mixture is subjected to ultrasound irradiation. The reaction mixture may be further agitated throughout the duration of the reaction by employing a rotary shaker, a magnetic stirrer, a centrifugal mixer, or an overhead stirrer. In another embodiment, the reaction mixture is left to stand (i.e. not stirred).

The compound of formula (I) may be isolated and purified by methods known to those of ordinary skills in the art, such as crystallization, filtration through a celite containing cartridge, evaporating the reaction mixture to dryness, aqueous work-up, extraction with organic solvents, distillation, column chromatography, and high pressure liquid chromatography (HPLC) on normal phase or reversed phase. Preferred methods include filtration and recrystallization. An isolated yield of the compound may be at least 70%, preferably at least 75%, preferably at least 80%, preferably at least 85%, preferably at least 90%, preferably at least 95%. As defined herein, a limiting reagent is determined as the starting reagent that is present in the smallest molar amount, including the aldehyde of formula (II), the compound of formula (III) and the compound of formula (IV). The isolated yield is calculated as (mole of the isolated compound/mole of the limiting reagent)×100%.

According to a second aspect, the present disclosure relates to a method of inhibiting corrosion of a metallic substrate in contact with a corrosive medium. The method involves mixing the compound of formula (I) of the first aspect in any of its embodiments with the corrosive medium in contact with the metallic substrate. Alternatively, the method may involve contacting and/or coating the metallic substrate with the compound of formula (I) prior to immersion into a corrosive environment. Preferably, the compound of formula (I) will be contacted with, or continuously or intermittently applied to, the surfaces of metallic substrates, preferably in a space or volume where continued contact between the metallic substrate and the compound can be maintained or refreshed.

As used herein, "corrosion" refers to the process which converts refined metals to their more stable oxide. It is the gradual loss of a material (usually metals) by chemical reaction with their environment. Commonly, this means electrochemical oxidation of metal in reaction with an oxidant such as oxygen. Rusting, the formation of iron oxides is a well-known example of electrochemical corrosion producing oxide(s) and/or salt(s) of the original metal. Corrosion degrades the useful properties of materials and structures including strength, appearance and permeability to liquids and gases. Many structural alloys corrode merely from exposure to moisture in air, but the process can be strongly affected by exposure to certain substances. Because corrosion is a diffusion-controlled process, it generally occurs on exposed surfaces.

As used herein, a "corrosion inhibitor" refers to a chemical compound or formulation that when added to a material and/or contacted with a corrodible substrate, typically a metal or an alloy, decreases the corrosion rates of the material. Inhibitors often play an important role in the oil extraction and processing industries where they have always been considered to be the first line of defense against corrosion. The compounds of the current disclosure may interact with the metallic substrate and form a cohesive and insoluble film on the surface of the substrate. An organic inhibitor that contains heteroatoms (e.g. N, O and S) may be adsorbed on a metallic surface thus blocking the active corrosion sites.

In one embodiment, the compound of formula (I) is adsorbed onto the metallic substrate through a chemisorption process which forms a protective film over the surface of the substrate. Substituents on the compound of formula (I) (e.g. $R_1$ and $R_3$) that demonstrate electron donating properties may enhance solubility of the compound in corrosive media, promote adsorption of the compound onto a metallic surface, thus leading to a greater corrosion inhibition capability of the compound. In one or more embodiments, the compound of formula (I) used herein has $R_1$ that is an electron-donating group (EDG), for example an alkoxy, an aryloxy, a dialkylamino, preferably a di($C_{1-8}$)alkylamino, preferably a di($C_{2-7}$)alkylamino, preferably a di($C_{3-6}$)alkylamino, preferably a di($C_{4-5}$)alkylamino, such as $-N(CH_3)_2$, $-N(CH_3)C_2H_5$, $-N(C_2H_5)_2$, pyrrolidinyl, piperidinyl, 4-methylpiperidinyl, morpholinyl, piperazinyl, and (N-methyl)piperazinyl. In a preferred embodiment, the compound of formula (I) used herein has $R_1$ as $-N(CH_3)_2$. In a most preferred embodiment, the compound of formula (I) used herein is The effectiveness of a corrosion inhibitor may depend on fluid composition, quantity of fluid and flow regime. The nature of a corrosion inhibitor may depend on the material being protected (most commonly metal objects) and the corrosive agent(s) in a corrosive medium to be neutralized.

As used herein, "parts per million" or "ppm" refers to an expression of concentration by mass or weight. For example, 1 ppm of a compound of formula (I) denotes a 1:1,000,000 weight ratio of the compound per total weight of fluid (e.g. liquids, gases or combinations thereof) contacting the metallic substrate. Alternatively, 1 ppm of a compound of formula (I) denotes a 1:1,000,000 weight ratio of the compound per total weight of fluid contained or carried within oil and gas infrastructure having the metallic substrates.

In one or more embodiments, the method disclosed herein involves introducing the compound of formula (I) in any of its embodiments into the corrosive medium at a concentration of 0.1-500 ppm, 1-300 ppm, 5-200 ppm, 10-150 ppm, 25-100 ppm, or 50-75 ppm. However, in certain embodiments, the compound of formula (I) may be introduced into the corrosive medium at a concentration less than 0.1 ppm or greater than 500 ppm.

Exemplary metallic substrates applicable to the present disclosure include, but are not limited to, copper, copper alloys (e.g. brass or bronze), aluminum, aluminum alloys (e.g. aluminum-magnesium, nickel-aluminum, aluminum-silicon), nickel, nickel alloys (e.g. nickel-titanium or nickel-chromium), iron, iron alloys, carbon steels, alloy steels, stainless steels, and tool steels.

Steel is an alloy of iron and carbon that is widely used in construction and other applications because of its high tensile strength and low cost. Carbon, other elements, and inclusions within iron act as hardening agents that prevent the movement of dislocations that naturally exist in the iron atom crystal lattices. The carbon in typical steel alloys may contribute up to 2.1% of its weight.

Steels can be broadly categorized into four groups based on their chemical compositions: carbon steels, alloy steels, stainless steels, and tool steels. Carbon steels contain trace amounts of alloying elements and account for 90% of total steel production. Carbon steels can be further categorized intro three groups depending on their carbon content: low carbon steels/mild steels contain up to 0.3% carbon, medium carbon steels contain 0.3-0.6% carbon, and high carbon steels contain more than 0.6% carbon. Alloys steels contain alloying elements (e.g. manganese, silicon, nickel, titanium, copper, chromium and aluminum) in varying proportions in order to manipulate the steel's properties, such as its hardenability, corrosion resistance, strength, formability, weldability or ductility. Stainless steels generally contain between 10-20% chromium as the main alloying element and are valued for high corrosion resistance. With over 11% chromium, steel is about 200 times more resistant to corrosion than mild steel. These steels can be divided into three groups based on their crystalline structure: austenitic steels, ferritic steels and martensitic steels. Tool steels contain tungsten, molybdenum, cobalt and vanadium in varying quantities to increase heat resistance and durability, making them ideal for cutting and drilling equipment.

In one embodiment, the metallic substrate comprises steel, carbon steel, low carbon steel, mild steel, medium carbon steel, high carbon steel, alloy steel, stainless steel, austenitic steel, ferritic steel, martensitic steel, tool steel, or mixtures thereof. Preferably, the metallic substrate comprises carbon steel. Most preferably the metallic substrate is a carbon steel with a carbon content in a range of 0.08-1.0%, preferably 0.09-0.5%, preferably 0.1-0.3%, or about 0.125%, for example, API 5 L X grade steel such as X52, X56, X60, X65, X70 to X120, N-80, J55, P-110, T-95, C1018, QT 800, and HS80, and other steel alloys such as 13Cr, 25Cr, Inconel 825, and 316 L.

As used herein, "systems" include, but are not limited to, systems used in petroleum (e.g., crude oil and its products) or natural gas production, such as well casing, transport pipelines, drilling and other oil field applications, transport, separation, refining, storage, and other liquid natural gas and petroleum-related applications, geothermal wells, water wells; cooling water systems including open recirculating, closed, and once-through systems; cisterns and water collection or holding systems, solar water heating systems, boilers and boiler water systems or systems used in power generation, mineral process waters including mineral washing, flotation and benefaction; paper mill digesters, washers, bleach plants, white water systems and mill water systems; black liquor evaporators in the pulp industry; gas scrubbers and air washers; continuous casting processes in the metallurgical industry; air conditioning and refrigeration systems; building fire protection heating water, such as pasteurization water; water reclamation and purification systems; membrane filtration water systems; food processing streams and waste treatment systems as well as in clarifiers, liquid-solid applications, municipal sewage treatment systems; and industrial or municipal water distribution systems.

In preferred embodiments, the metallic substrate is part of a system for oil or gas production, transportation, or refining. The metallic substrate may be part of a system used in the drilling, petroleum, oil and gas industries including drills, drill bits, pumps, compressors, pipelines, and other tools and equipment, electric parts such as transformers, power generators and electric motors, vehicle parts including those of boats, autos, trucks, aircraft, and military vehicles. Tools, including construction, automotive, household, and kitchen tools, are included.

The method disclosed herein in any its embodiments may be effective in protecting the aforementioned metallic substrate against corrosion in various environments such as acidic and/or high salt concentration environments. In one or more embodiments, the corrosive medium contains at least one acid. The acid may be in liquid or gas forms and include, but are not limited to, inorganic acids such as carbon dioxide ($CO_2$), hydrochloric acid (HCl), sulfuric acid ($H_2SO_4$), nitric acid ($HNO_3$), hydrofluoric acid (HF), phosphoric acid, and hydrogen sulfide ($H_2S$), as well as organic acids such as acetic acid ($CH_3COOH$), formic acid (HCOOH), and citric acid. These acids may be present in the aqueous corrosive medium at saturated concentrations, or at a concentration in a range of 0.001-10 M, 0.01-8 M, 0.1-6 M, 0.2-4 M, 0.4-2 M, or 0.5-1 M. In at least one embodiment, the corrosive medium contains $CO_2$. In a preferred embodiment, the corrosive medium has a pH of 5 or below, for example, a pH in a range of 1-5, 1.5-4.75, 2-4.5, 2.5-4.25, 3-4, 3.25-3.9, or about 3.8.

Inorganic salts such as sodium chloride have been known to cause serious corrosion to steels. As used herein, brine is an aqueous mixture of one or more soluble salts (e.g. sodium chloride, potassium chloride, calcium chloride, calcium bromide, sodium bromide, potassium bromide, zinc bromide, magnesium chloride). Seawater or water from a salt lake may be considered a brine. In one or more embodiments, brine may be present in the corrosive medium. For example, the aqueous corrosive medium may contain 1-10 wt %, 2-8 wt %, or 3-5 wt % sodium chloride, 0.1-0.8 wt %, 0.15-0.6 wt %, or 0.2-0.4 wt % calcium chloride, as well as 0.05-0.7 wt %, 0.1-0.5 wt %, or 0.15-0.25 wt % magnesium chloride, each relative to a total weight of the corrosive medium. In certain embodiments, the corrosive medium contains the acid, preferably $CO_2$, and brine.

In one embodiment, the corrosive medium is agitated. For example, the corrosive medium may be agitated by using a rotator with a rotational speed of at least 500 rpm, preferably at least 800 rpm, more preferably at least 1,000 rpm. In another embodiment, the corrosive medium is left to stand without being stirred.

Corrosion rate is the speed at which metals undergo deterioration within a particular environment. The rate may depend on environmental conditions and the condition or type of metal. Factors often used to calculate or determine corrosion rate include, but are not limited to, weight loss (reduction in weight during reference time), area (initial surface area), time (length of reference time) and density. Corrosion rate is typically computed using mils per year (mpy). Mils penetration per year (mpy) is a unit of measurement equal to approximately one thousandth of an inch. The unit is typically applied in industries like manufacturing and engineering to measure coating thickness or tolerance. Mils penetration per year is commonly referred to as mil in the U.S. measurement system.

In one or more embodiments, the compound of formula (I) of the present disclosure in any of its embodiments imparts a corrosion rate in a range of 0.5-2.5 mils penetration per year (mpy) to the metallic substrate, preferably 0.6-2.4 mpy, preferably 0.8-2.3 mpy, preferably 1-2.2 mpy, preferably 1.1-2.1 mpy, preferably 1.2-2 mpy, preferably 1.3-1.8 mpy, preferably 1.5-1.7 mils penetration per year (mpy).

In a preferred embodiment, the corrosion rate of the metallic substrate according to the presently disclosed method may be slowed by at least 18 mpy relative to the corrosion rate of a substantially identical metallic substrate exposed to a substantially identical corrosive medium lacking the compound of formula (I) (e.g. compound PP), preferably slowed by 18.5-25 mpy, 19-22 mpy, or 19.8-21 mpy relative to the corrosion rate of a substantially identical metallic substrate exposed to a substantially identical corrosive medium lacking the compound of formula (I) (see Table 2).

Corrosion inhibition efficiencies (IE %) may be measured with the Tafel extrapolation, electrochemical impedance spectroscopy (EIS), linear polarization resistance (LPR), potentiodynamic polarization (PDP), gravimetric or other similar methods. In one or more embodiments, the method described herein in any of its embodiments achieves a corrosion inhibition efficiency in a range of 80-99%, 85-98%, 90-97%, 91-96%, 92-95%, or 93-94%.

In a preferred embodiment, the method disclosed herein has a corrosion inhibition efficiency in a range of 80-95% when the compound of formula (I) is introduced into the corrosive medium at a concentration ranging from 5-50 ppm, preferably a corrosion inhibition efficiency greater than 90% at a concentration of up to 45 ppm, preferably greater than 90% IE at a concentration of up to 40 ppm, preferably greater than 90% IE at a concentration of up to 35 ppm, preferably greater than 90% IE at a concentration of up to 30 ppm, preferably greater than 90% IE at a concentration of up to 25 ppm, preferably greater than 90% IE at a concentration of up to 20 ppm, preferably greater than 90% IE at a concentration of up to 15 ppm, preferably greater than 90% IE at a concentration of up to 10 ppm, preferably greater than 90% IE at a concentration of up to 5 ppm (see Tables 1 and 2).

The examples below are intended to further illustrate protocols for preparing, characterizing the compound of formula (I), and uses thereof, and are not intended to limit the scope of the claims.

Example 1

Synthesis and Characterization of 5-(4-(dimethylamino)phenyl)-2,7-dithioxo-2,3,5,6,7,8-hexahydropyrimido[4,5-d]pyrimidin-4(1H)-one (PP)

Figure 1:
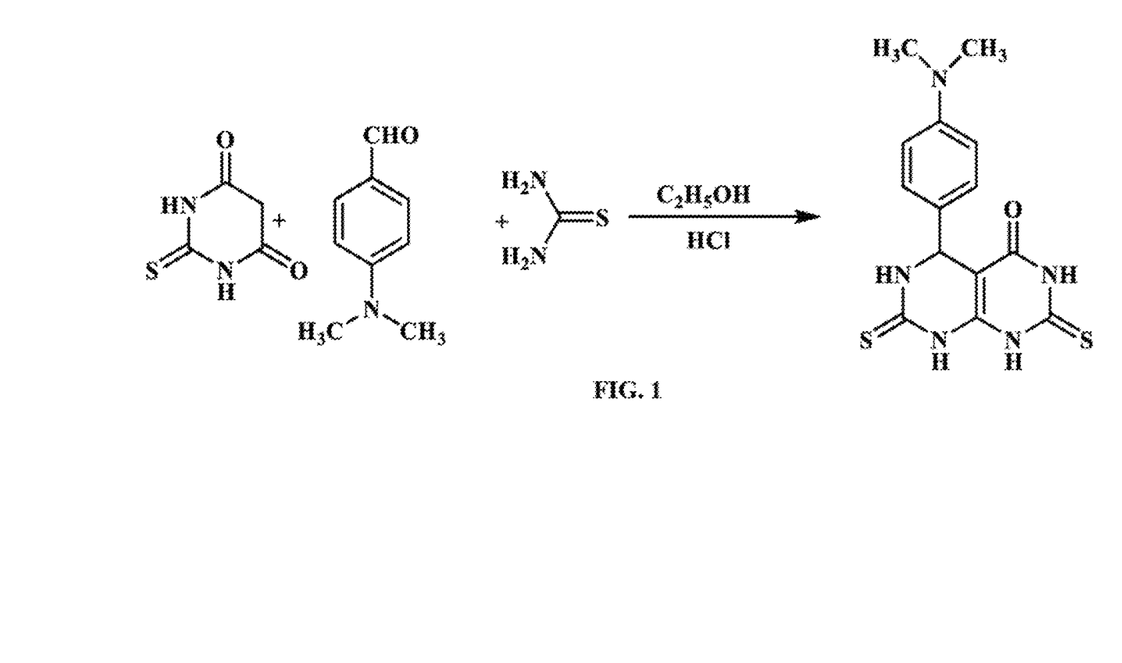
FIG. 1 shows a synthesis procedure for a compound (PP) of formula (I).

A mixture of 2-thiobarbituric acid (0.01 mol), dimethylaminobenzyldehyde (0.01 mol), thiourea (0.01 mol), absolute ethanol (10 ml) and 36% HCl (3 mL) are taken in a round bottom flask and heated under reflux for 4 h. The reaction mixture was then allowed to cool. A red precipitate formed was filtered off and crystallized in ethanol. The molecular structure of the inhibitor was confirmed by IR and $^1$H NMR. FIG. 1 shows the synthesis of inhibitor (PP). Detailed characterizations are as follows: δH (DMSO-d$_6$): 3.0 (d, 1H, H-5), 3.1 (s, 6H, N-CH3), 7.0-7.6 (m, 4H, Ar—H), 8.2, 8.5 (s, 2H, NH), 11.6 (s, 1H, N—H), 12.1 (s, 1H, N—H) ppm. IR (KBr) $v_{max}$: 3213 (NH), 3062, 2908 (CH3), 1680 (C=O), 1481 (CH Aromatic), 1362, 1300 (C=S), 1237 (aromatic shoulder), 1185, 1072, 969, 857, 817, 790, and 723 (CH aromatic) cm-1. Melting point: 254-256° C.

Example 2

Materials

The NACE ID196 brine solution containing 3.5 wt % NaCl, 0.305 wt % CaCl$_2$.2H$_2$O, and 0.186 wt % MgCl$_2$.6H$_2$O was prepared with double distilled water [M. V. Azghandi, A. Davoodi, G. A. Farzi, et al., Water-base acrylic terpolymer as a corrosion inhibitor for SAE1018 in simulated sour petroleum solution in stagnant and hydrodynamic conditions, Corrosion Science 64 (2012) 44-54]. The elemental composition (wt. %) of the API X60 cylindrical pipeline steel was summarized below: C (0.125), Si (0.52), Mn (1.83), Cr (0.121), Cu (0.296), W (0.134), Ni (0.091), Mo (0.079), Al (0.043), Sn (0.081), Nb (0.053), V (0.078), Pb (0.030), Zn (0.032), and Fe (<96.2). The steel sample was prepared by abrading to a final 800 grit size using silicon carbide paper, followed by washing thoroughly with double distilled water, ultrasonic vibration in acetone, with subsequent mechanical drying.

Example 3

Electrochemical Measurements

The electrochemical techniques used include electrochemical impedance spectroscopy (EIS), linear polarization resistance (LPR) and potentiodynamic polarization (PDP). The measurements were performed at room temperature using a Gamry Potentiostat/Galvanostat/ZRA (reference 600+) equipped with the Gamry framework system based on ESA410. The Gamry applications included software like EIS300 for EIS measurements and Echem Analyst 6.0 software package for data fitting. The corrosion testing was conducted in a 250 mL corrosion cell with compartments for Ag/AgCl (3 M KCl) as reference electrode, graphite rod as counter electrode, purge gas tube for CO$_2$ and the API X60 RCE as working electrode. The working electrode area was 3.14 cm$^2$. Hydrodynamic condition at 1000 rpm rotation speed was applied with the aid of a Gamry speed rotator (model RDE 710 Rotating Electrode). Before mounting the working electrode, the brine solution was saturated with CO$_2$ gas by purging under 1 atm partial pressure for 1 h, ensuring a pH of 3.83. The corrosion inhibitor was injected into the solution immediately after the working electrode was mounted while the CO$_2$ gas was bubbled continuously throughout the experiment. The inhibitor concentration was varied at 5, 10, and 50 ppm. The electrochemical measurements were preceded by 1 h of free corrosion in order for the working electrode to attain an open circuit potential (OCP). EIS was carried out in the frequency range of 100 kHz to 0.1 Hz using a voltage amplitude of 10 mV. LPR measurement was performed within ±10 mV of the OCP value using a scan rate of 0.167 mV/s, and polarization resistance ($R_n$) value was subsequently calculated from the LPR measurement by assuming anodic and cathodic Tafel constants of 120 mV/decade [M. Stern, A. L. Geary, Electrochemical polarization I. A theoretical analysis of the shape of polarization curves, J. Electrochemical Society 104 (1957) 56-63]. The PDP measurement was recorded within potential range of ±300 mV with respect to the OCP by applying a scan rate of 0.5 mV/s. Polarization parameters such as corrosion potential ($E_{corr}$) and corrosion current density ($i_{corr}$) were derived based on the Tafel extrapolation method. Inhibition efficiency (IE %) values were calculated from the electrochemical measurements using the stated equations:

$$IE_{EIS/LPR} = 1 - \frac{R_{p(blank)}}{R_{p(inh)}} \times 100\%; \tag{6}$$

where $R_{p(blank)}$ and $R_{p(inh)}$ are, respectively, the polarization resistance recorded in the absence and presence of an inhibitor.

$$IE_{PDP} = 1 - \frac{i_{corr(inh)}}{i_{corr(blank)}} \times 100\%; \tag{7}$$

where $i_{corr\,(blank)}$ and $i_{corr\,(inh)}$ are, respectively, the corrosion current density recorded in the absence and presence of an inhibitor.

Example 4

Surface Characterization

In order to see the extent of surface microstructural damage of the steel due to the CO$_2$ corrosion, and the effect of the PP inhibitor on the phenomenon, the surface morphology of the API X60 steel was viewed with a scanning electron microscope (SEM JEOL JSM-6610 LV) after corrosion in the CO$_2$-saturated NACE brine solution without and with the optimum (50 ppm) concentration of PP. XRD was also applied to characterize the phase composition of the steel surface before and after corrosion in the inhibited and uninhibited CO$_2$-saturated brine solution, using the Rigaku-Ultima IV-X-ray diffractometer. In addition, ATR-IR spectra of the steel sample after the CO$_2$ corrosion in the brine solution without and with 50 ppm of PP inhibitor were acquired in the range of 400-4000 cm$^{-1}$ using an IR reflectance spectrophotometer (PerkinElmer, Spectrum One, universal ATR attachment with a diamond and ZnSe crystal, The Netherlands).

Example 5

Electrochemical Impedance Spectroscopy (EIS)

Figure 2A:
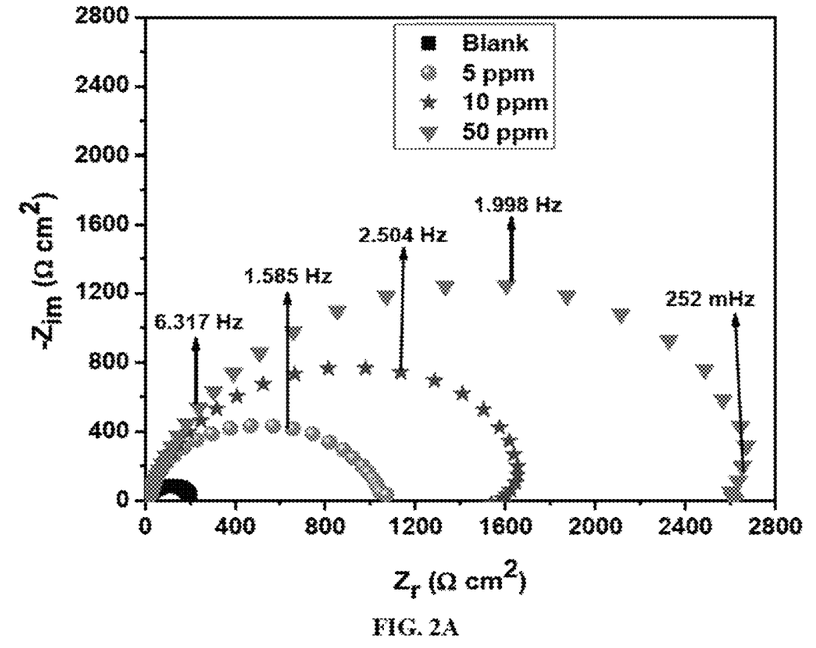
FIG. 2A is an overlay of Nyquist plots for X60 steel measured in $CO_2$-saturated brine in the absence (blank) or presence of compound PP at 5, 10, and 50 ppm, respectively.
Figure 2B:
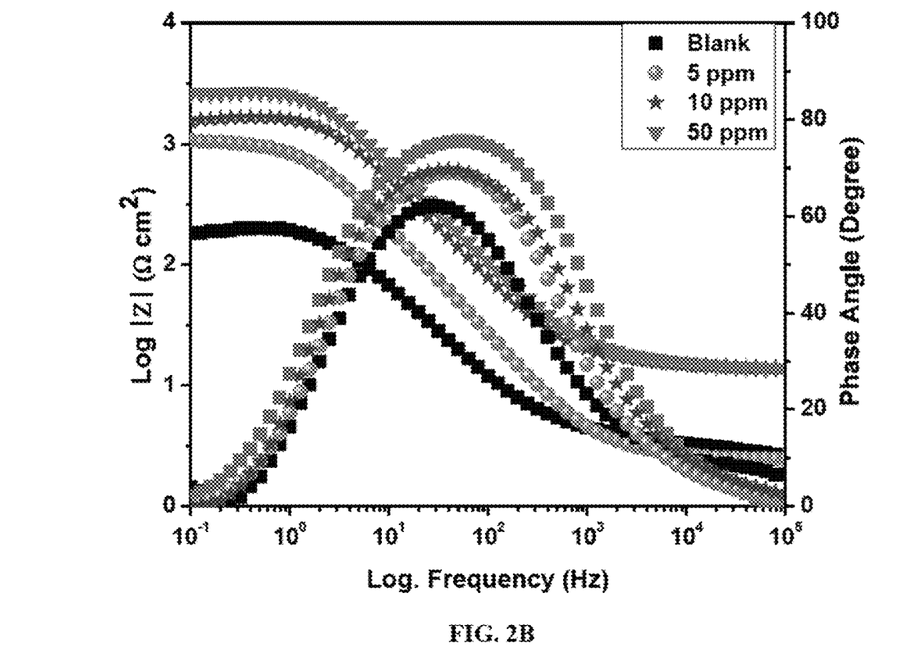
FIG. 2B is an overlay of Bode plots for X60 steel measured in $CO_2$-saturated brine in the absence (blank) or presence of compound PP at 5, 10, and 50 ppm, respectively.

The Nyquist and Bode plots obtained for the X60 steel in the $CO_2$-saturated NACE brine solution without and with different PP concentrations under 1000 rpm rotation speed, are provided in FIGS. 2A and 2B. In the Nyquist plots shown by FIG. 2A, the steel sample displays single depressed semicircle both in the absence and presence of the PP inhibitor. This is indicative of corrosion phenomena controlled strictly by charge transfer processes [M. Mandavian, S. Ashhari, Corrosion inhibition performance of 2-mercaptobenzimidazole and 2-mercaptobenzoxazole compounds for protection of mild steel in hydrochloric acid solution, Electrochimica Acta 55 (2010) 1720-1724]. The size of the semicircle is greater in the inhibited brine solution than in the blank solution, and increasing PP concentration clearly results in larger semicircle size. Since the size of the Nyquist semicircle usually correlates with the corrosion resistance of the metallic material, it implies that the PP is an effective inhibitor for the $CO_2$ corrosion of the X60 steel in the NACE brine solution. Although the formation of $FeCO_3$ scale can increase the corrosion resistance of steel during $CO_2$ corrosion [S. Nesic, K. J. Lee, The mechanistic model of iron carbonate film growth and the effect on $CO_2$ corrosion of mild steel, CORROSION/02 (Houston, Tex.: NACE International, 2002) 1-35], such chemistry cannot be guaranteed in the present corrosion environment with measured pH value of 3.83 [S. Nesic, J. Postlethwaite, S. Olsen, An electrochemical model for prediction of corrosion of mild steel in aqueous carbon dioxide solutions, Corrosion 52 (1996) 280-294]. The observed corrosion inhibition provided by the PP inhibitor is, therefore, due to the inhibitor adsorption on the steel surface which blocks off reactive sites from the attack by the weak $H_2CO_3$ acid and the aggressive $Cl^-$ species in the brine solution.

TABLE 1

EIS parameters for X60 steel after $CO_2$ corrosion in NACE brine under 1000 rpm without and with different PP concentration.

| Conc. (ppm) | $R_s$ ($\Omega\ cm^2$) | $Y_0$ (F $cm^{-2}$ $s^{n-1}$) | n | $C_{dl}$ ($\mu F\ cm^{-2}$) | $R_{ct}$ ($\Omega\ cm^2$) | IE % |
|---|---|---|---|---|---|---|
| Blank | 3.130 | 407 | 0.8 | 224 | 185 | — |
| 5 | 2.533 | 113 | 0.9 | 90 | 1044 | 82 |
| 10 | 1.473 | 45 | 0.9 | 34 | 1715 | 89 |
| 50 | 1.470 | 36 | 0.9 | 28 | 2807 | 93 |

Figure 2C:
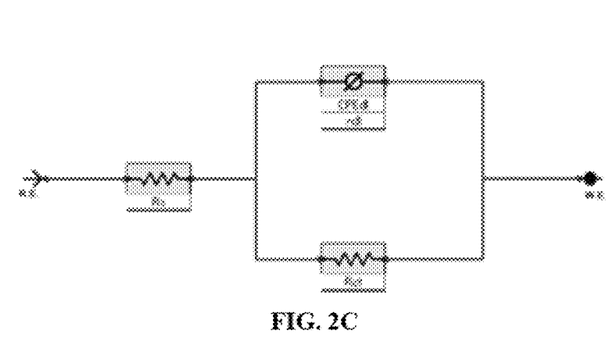
FIG. 2C shows an equivalent circuit model adopted by the current disclosure.

The corresponding Bode phase angle plots in FIG. b reveals single impedance maxima for the steel sample in the $CO_2$-saturated NACE brine solution without and with different concentrations of PP. This supports the suggestion that no well-developed corrosion product layer has been formed on the steel surface at this time, both in the inhibited and uninhibited solutions. Increasing PP concentration again results in higher phase angle peaks, as well as higher absolute impedance values. Hence, the mechanism of $CO_2$ corrosion of X60 steel in the NACE brine solution without and with PP inhibitor under 1000 rpm rotation is controlled by the dielectric and charge transfer properties of the electric double layer at the steel-brine solution interface. The equivalent circuit in FIG. 1c has, therefore, been adopted to provide electrical interpretation for the corrosion behavior after modeling with the Echem Analyst 6.0 software. Such circuit has been used previously to model similar impedance phenomena [I. B. Obot, Ikenna B. Onyeachu, A. MadhanKumar, Sodium alginate: A promising biopolymer for corrosion protection of API X60 high strength carbon steel in saline medium, Carbohydrate Polymers 178 (2017) 200-208; and D. I. Njoku, Y. Li, H. Lgaz, et al., Dispersive adsorption of *Xylopia aethiopica* constituents on carbon steel in acid-chloride medium: A combined experimental and theoretical approach. J. Molecular Liquids 249 (2018) 371-388]. The equivalent circuit comprises a solution resistance ($R_s$) connected to a constant phase element ($CPE_{dl}$) which is in parallel with a charge transfer resistance ($R_{ct}$). The constant phase element (CPE) with exponent, n, is used in the model instead of a pure capacitor so as to compensate for the surface inhomogeneity of solid electrode materials which usually exhibit frequency dependent dispersions. The impedance of a CPE, $Z_{CPE}$, is given according to the following equation:

$$Z_{CPE} = Y_0^{-1} (j\omega)^{-n} \qquad (8);$$

whereby j is an imaginary number $$\left(j = (-1)^{\frac{1}{2}}\right),$$

$Y_0$ represents the magnitude of the CPE, $\omega$ is the angular frequency (rad/s) and n ($-1 \leq n \leq 1$) is the CPE power. On the other hand, the double layer capacitance ($C_{dl}$) was calculated based on the following equation:

$$C_{dl} = Y_o (2\pi f_{max})^{n-1} \qquad (9);$$

whereby $f_{max}$ is the frequency (Hz) corresponding to the maximum impedance of the imaginary component in the Nyquist plot.

The values of electrical elements derived from the equivalent circuit model are presented in Table 1. The Table 1 reveals that double layer capacitance ($C_{dl}$) decreases with increasing PP concentration, which indicates greater displacement of water molecules from the steel-solution interface leading to decreased corrosion rate. This can also be confirmed by the steady increase in both $R_{ct}$ and inhibition efficiency (IE %) values as PP concentration increases. More so, the hydrodynamic effect of rotation applied during this study is liable to augment the transport of PP molecules from the solution bulk to the steel surface for enhanced adsorption and subsequent corrosion inhibition.

Example 6

Potentiodynamic Polarization and Linear Polarization Resistance

Figure 3:
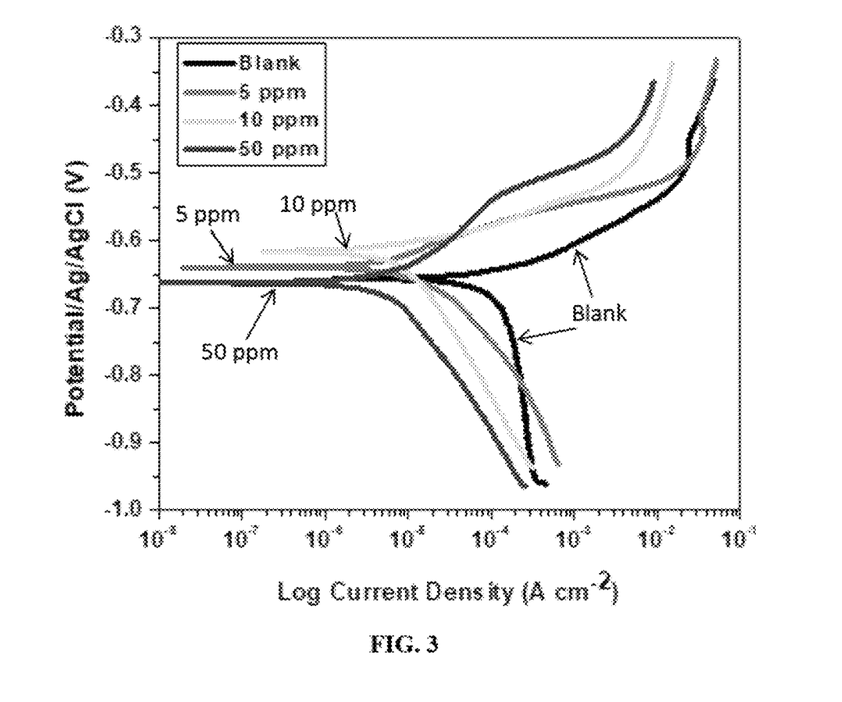
FIG. 3 is an overlay of potentiodynamic polarization curves for X60 steel measured in $CO_2$-saturated brine in the absence (blank) or presence of compound PP at 5, 10, and 50 ppm, respectively.

FIG. 2 shows the potentiodynamic polarization curves obtained for the X60 steel during $CO_2$ corrosion in the NACE brine solution under 1000 rpm without and with different PP concentrations. It is obvious that the PP inhibitor concentration had no clear effect on the corrosion potential of the steel in the brine solution. However, the addition of the PP inhibitor clearly decreased both anodic and cathodic currents throughout the applied potential perturbation range. This decrease is more pronounced as PP concentration reached 50 ppm. The PP inhibitor, therefore, functions as a mixed-type corrosion inhibitor; adsorbing on the steel surface to retard the rates of both anodic Fe dissolution and cathodic $H^+$ reduction. No clear phenomenon of passivation is noticed during the polarization, which supports the one time-constant displayed in the EIS measurement. The electrical parameters obtained from the PDP measurement are provided in Table 2. The addition of PP into the NACE brine solution lowers the corrosion current density ($i_{corr}$) of the X60 steel from 106 µA cm$^{-2}$ in the blank solution to 5.380 µA cm$^{-2}$ with 95% inhibition efficiency in the presence of the optimum 50 ppm of inhibitor. Table 2 also contains the values of polarization resistance ($R_p$), corrosion rates (CR) expressed in mpy and corresponding IE % derived from the LPR measurements. The LPR, acquired within ±10 mV of the OCP, is a direct current technique which operates safely to provide accurate instantaneous information concerning the steel corrosion. The values and trend of the IE % determined from LPR measurement are highly consistent with the values obtained from the EIS and PDP measurements.

compared with the uninhibited solution where the Fe (110) intensity is higher and signifies greater exposure of unprotected Fe atoms.

Figure 6A:
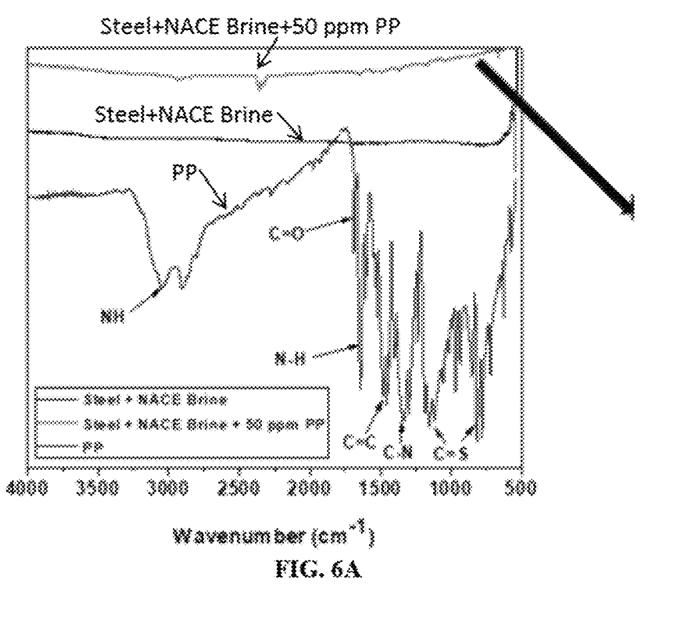
FIG. 6A is an overlay of ATR FT-IR spectra of compound PP, and surface of X60 steel after immersing in $CO_2$-saturated brine in the absence or presence of compound PP at 50 ppm.

ATR-IR characterization was employed to understand the active centers on the inhibitor which facilitated the binding and eventual protection of the steel during the $CO_2$ corrosion. The ART-IR spectra for the pure PP inhibitor and the steel surface after corrosion in the $CO_2$-saturated NACE brine solution without and with the 50 ppm of PP inhibitor are presented in FIG. 5. The pure PP inhibitor shows a doublet peak around 3200 cm$^{-1}$ with corresponding in-plane bending peak around 1600 cm$^{-1}$ which indicate the presence of amine (NH) functional group [D. Boinnard, P. Cassoux, V. Petrouleas, et al., Iron (II) complexes of 2,2'-biimidazole

TABLE 2

Polarization parameters for X60 steel after $CO_2$ corrosion in NACE brine under 1000 rpm without and with different PP concentration.

| | PDP | | | | LPR | | | |
|---|---|---|---|---|---|---|---|---|
| Conc. (ppm) | $E_{corr}$ (mV/Ag/AgCl) | $i_{corr}$ (µA/cm$^2$) | $\beta_a$ (mV/Decade) | IE % | $E_{corr}$ (mV/Ag/AgCl) | $R_p$ (Ω cm$^2$) | IE % | CR (mpy) |
| Blank | −664 | 106.0 | 359 | — | −660 | 180 | — | 21.060 |
| 5 | −639 | 7.670 | 60 | 93 | −635 | 1551 | 88 | 2.445 |
| 10 | −616 | 6.500 | 49 | 94 | −626 | 1653 | 89 | 2.293 |
| 50 | −662 | 5.380 | 53 | 95 | −666 | 2976 | 94 | 1.274 |

Example 7

Surface Characterization

Figure 4A:
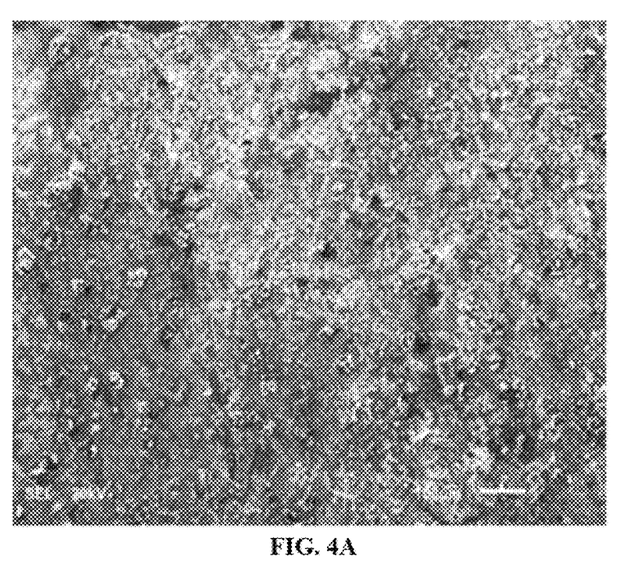
FIG. 4A is a scanning electron microscopy (SEM) micrograph showing the surface morphology of X60 steel after immersing in $CO_2$-saturated brine in the absence of compound PP.
Figure 4B:
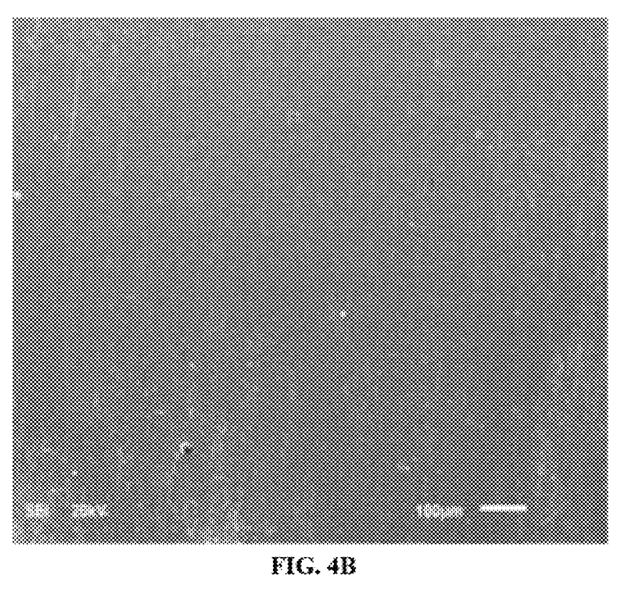
FIG. 4B is a scanning electron microscopy (SEM) micrograph showing the surface morphology of X60 steel after immersing in $CO_2$-saturated brine in the presence of compound PP at 50 ppm.

The electrochemical measurements reveal that the addition of PP decreases the corrosion rate of the X60 steel in the $CO_2$-saturated NACE brine solution, and that the highest inhibition efficiency occurred in the presence of 50 ppm inhibitor, given the range of concentrations tested. The SEM surface micrographs of the steel sample after corrosion in the $CO_2$-saturated brine solution without and with 50 ppm PP inhibitor are, therefore, shown in FIG. 3. The steel sample which corroded in the blank solution, FIG. 3*a*, exhibits a highly rough surface showing greater extent of corrosion attack. On the contrary, FIG. 3*b* shows that the steel sample surface is smoother in the inhibited brine solution containing 50 ppm of PP inhibitor. This observation strongly confirms that the PP adsorption effectively blocks off the contact between the steel surface and the corrosion agents in the brine solution.

Figure 5A:
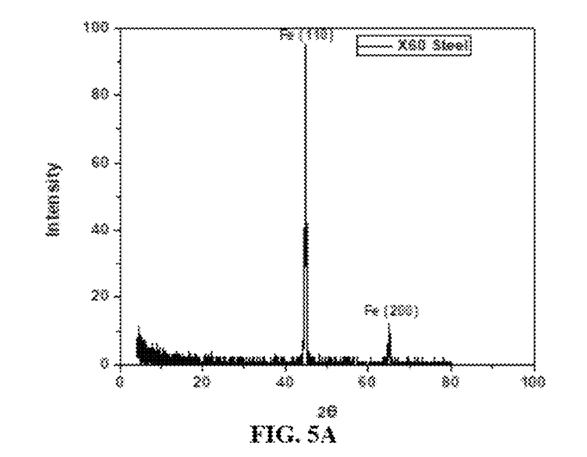
FIG. 5A is an X-ray diffraction (XRD) diffractogram of X60 steel before immersing in $CO_2$-saturated brine.
Figure 5B:
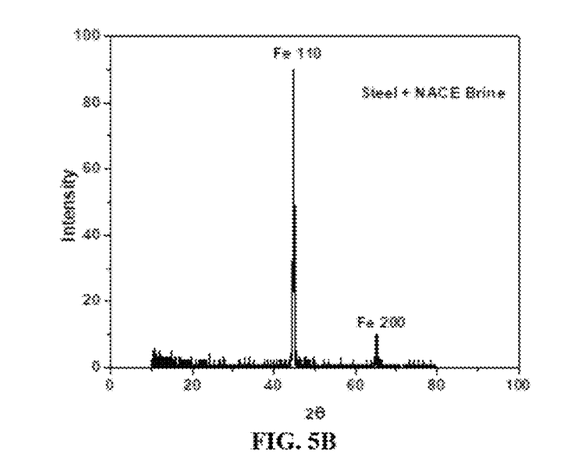
FIG. 5B is an XRD diffractogram of X60 steel after immersing in $CO_2$-saturated brine in the absence of compound PP.
Figure 5C:
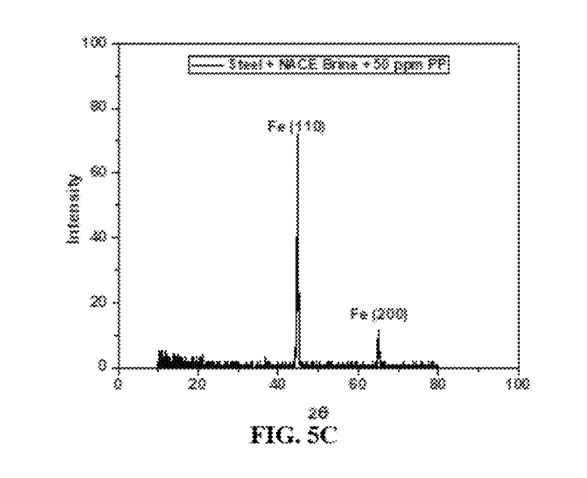
FIG. 5C is an XRD diffractogram of X60 steel after immersing in $CO_2$-saturated brine in the presence of compound PP at 50 ppm.

FIG. 4 shows corresponding XRD characterization of the steel sample before and after corrosion in the inhibited and uninhibited $CO_2$-saturated NACE brine solution. Only the Fe (110) and Fe (200) crystal phases are detected on the steel sample before and after corrosion testing. When the intensities of both Fe phases are compared, a noticeable decrease in the intensity of Fe (110) phase could be observed after the steel corroded in the inhibited solution (FIG. 4*c*), compared with the uninhibited solution (FIG. 4*b*). Any change in the intensity of Fe (200) was quite insignificant. This indicates that the Fe (110) phase is the most energetically favorable phase with which the X60 steel interacts with the brine solution and the inhibitor molecule. Therefore, the adsorption of the PP molecules on the Fe (110) atoms in the steel matrix masks their activity and inhibits their participation in the corrosion process. This is the reason that the corrosion rate of the steel decreased in the presence of the PP inhibitor, and 2,2'-bibenzimidazole as models of the photosynthestic mononuclear non-heme ferrous sites. Synthesis, molecular and crystal structure, and Moessbauer and magnetic studies, Inorganic Chemistry 29 (1990) 4114-4122, incorporated herein by reference in its entirety]. A weak singlet peak occurs around 1680 cm$^{-1}$ and has been attributed to the carbonyl (C=O) group in the molecule [Y. Zhang, H. Yin, Q. Zhang, et al., A novel polyaspartic acid derivative with multifunctional groups for scale inhibition application, J. Environmental Technology 39 (2017) 843-850, incorporated herein by reference in its entirety], while the thiocarbonyl (C=S) group exhibits characteristic absorption peaks around 1100 cm$^{-1}$ and 800 cm$^{-1}$ [M. A. Nabar, Infrared Absorption Spectral Studies of the Complexes with Substituted 2-Thioureas. I. Bis (1-phenyl-2-thiourea) copper (I) Chloride. Bulletin of the Chemical Society of Japan 39 (1966) 1067-1069, incorporated herein by reference in its entirety]. The C=C stretching peak corresponding to the aromatic ring is observed between 1480 and 1400 cm$^{-1}$. After the steel corrosion in the inhibited brine solution, the peaks corresponding to NH functional group can still be observed as the most prominent peaks, occurring around 32000 cm$^{-1}$ and 1600 cm$^{-1}$ (shown clearly in the enlarged form). It suggests that the PP inhibitor adsorbs onto the X60 steel surface using its amine nitrogen atoms in the pyrimidine molecule. Interestingly, a doublet peak is obvious around 2350 cm$^{-1}$, which was not noticed for the steel sample after corrosion in the blank solution, as well as for the pure PP. Such peak has been attributed to the adsorption of $CO_2$ [ O. S. Galvez, B. Mate, V. J. Herrero et al., Trapping and adsorbing of CO in amorphous ice: A FTIR study. Icarus, Elsevier 197(2) (2008) 599].

Figure 6B:
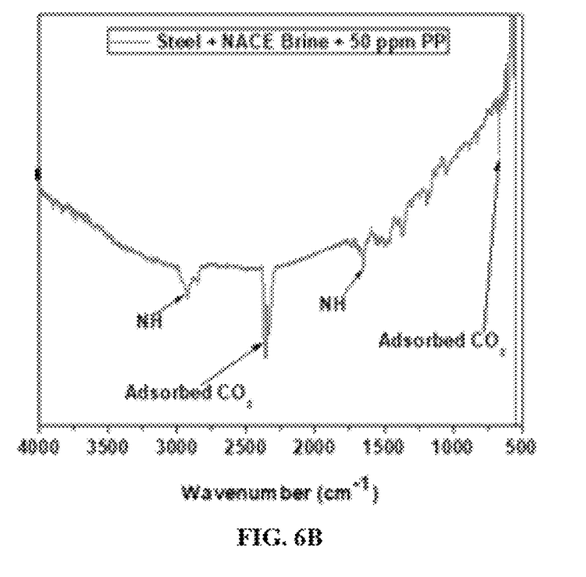
FIG. 6B is an expanded view of the ATR FT-IR spectrum of surface of X60 steel after immersing in $CO_2$-saturated brine in the presence of compound PP at 50 ppm.

According to literature, two IR peaks are possible for $CO_2$, one at 2350 cm$^{-1}$ and the other at 666 cm$^{-1}$. The absorption at 2350 cm$^{-1}$ is attributed to the asymmetric vibration which causes a change in the dipole moment of the $CO_2$ molecule, while the absorption at 666 cm$^{-1}$ is attributed to the two bending vibrational modes of $CO_2$ which are identical in energy. These peaks are not observed for the steel which corroded in the blank solution. Since the PP inhibitor adsorbs onto the steel surface using its nitrogen atoms and the $CO_2$ must exist in the aqueous form in the corrosion system, we suspect, at this time, an entrapment of $CO_{2(aq)}$ within the growing layer of the adsorbed inhibitor, which may be a preliminary step towards the nucleation of carbonate corrosion products on the steel surface, which further provides corrosion resistance to the steel.

Example 8

A one-pot multicomponent reaction based on the principle of green chemistry was used for the synthesis of a pyrimidine compound. Characterization of the synthesized inhibitor, 5-(4-(dimethylamino)phenyl)-2,7-dithioxo-2,3,5,6,7,8-hexahydropyrimido[4,5-d]pyrimidin-4(1H)-one (PP), was performed using nuclear magnetic resonance ($^1$H NMR) and FTIR spectroscopies.

In the present disclosure, dimethylamino benzaldehyde has been specifically chosen as one of the reactants to provide high electron density at nitrogen atom to facilitate its adsorption onto metal surface. This pyrimidine has been evaluated as potential inhibitor for the $CO_2$ corrosion of API X60 steel in NACE ID196 brine solution at room temperature. The performance of the synthesized pyrimidine-derivative as a corrosion inhibitor has been assessed with electrochemical and surface characterization methods. For this purpose, a rotating cylinder electrode (RCE) was applied under a rotation speed of 1000 rpm to simulate a turbulent flow condition, which is a common flow condition found in oilfield environments. Electrochemical techniques like electrochemical impedance spectroscopy (EIS), linear polarization resistance (LPR), and potentiodynamic polarization (PDP) complemented with surface characterization techniques (SEM and ATR-IR) and phase characterization technique (XRD) were utilized for electrochemical analysis. Compound PP has shown to be an effective corrosion inhibitor (93% IE at 50 ppm). In addition, the inhibition efficiency of PP was observed to increase with concentration. Compound PP may bind onto the steel surface via the amine group present in the pyrimidine structure.

The invention claimed is:

1. A compound of formula (I)

a salt thereof, a solvate thereof, a tautomer thereof, a stereoisomer thereof, or a mixture thereof.

2. A method of inhibiting corrosion of a metallic substrate in contact with a corrosive medium, the method comprising:
introducing the compound of formula (I) of claim 1 into the corrosive medium in contact with the metallic substrate.

3. The method of claim 2, wherein the metallic substrate comprises steel.

4. The method of claim 2, wherein the metallic substrate comprises carbon steel.

5. The method of claim 2, wherein the corrosive medium comprises at least one inorganic acid, at least one inorganic salt, or both.

6. The method of claim 5, wherein the corrosive medium comprises $CO_2$, brine, or both.

7. The method of claim 2, wherein the corrosive medium has a pH of 5 or below.

8. The method of claim 2, wherein the compound of formula (I) is introduced into the corrosive medium at a concentration of 0.1-200 ppm.

9. The method of claim 2, which has a corrosion inhibition efficiency in a range of 85-98%.

10. The method of claim 2, wherein the compound of formula (I) imparts a corrosion rate in a range of 0.8-2.5 mils penetration per year (mpy) to the metallic substrate.

11. The method of claim 2, wherein the metallic substrate is part of a system for oil or gas production, transportation, or refining.

* * * * *